(12) United States Patent
Nguyen et al.

(10) Patent No.: US 11,766,666 B2
(45) Date of Patent: Sep. 26, 2023

(54) CATALYST FOR CONVERTING LIGHT OLEFIN TO AROMATICS, METHOD OF MAKING AND METHOD OF USING THE SAME

(71) Applicants: China Energy Investment Corporation Limited, Beijing (CN); National Institute of Clean-and-Low-Carbon Energy, Beijing (CN)

(72) Inventors: Lisa Nguyen, Santa Clara, CA (US); Hui Wang, Fremont, CA (US); Junjun Shan, San Jose, CA (US); Louis Guillen, San Jose, CA (US); Hua Liu, Beijing (CN); Aihua Zhang, San Bruno, CA (US); Joshua Miles, San Francisco, CA (US)

(73) Assignees: CHINA INVESTMENT CORPORATION LIMITED, Beijing (CN); NATIONAL INSTITUTE OF CLEAN-AND-LOW-CARBON ENERGY, Beijing (CN)

( * ) Notice: Subject to any disclaimer, the term of this patent is extended or adjusted under 35 U.S.C. 154(b) by 0 days.

(21) Appl. No.: 17/137,868

(22) Filed: Dec. 30, 2020

(65) Prior Publication Data
US 2022/0203343 A1 Jun. 30, 2022

(51) Int. Cl.
*B01J 29/46* (2006.01)
*B01J 27/185* (2006.01)
(Continued)

(52) U.S. Cl.
CPC .............. *B01J 29/46* (2013.01); *B01J 21/04* (2013.01); *B01J 27/1853* (2013.01);
(Continued)

(58) Field of Classification Search
CPC .. B01J 37/0009; B01J 2229/18; B01J 29/061; B01J 29/405; B01J 23/8906; B01J 27/22;
(Continued)

(56) References Cited

U.S. PATENT DOCUMENTS 8,772,563 B2 7/2014 Lauritzen et al.
8,946,107 B2 2/2015 Lauritzen et al.
(Continued)

FOREIGN PATENT DOCUMENTS

EP 0785178 A1 7/1997

OTHER PUBLICATIONS

Qingzhu et al., "Study on the hydroaromatization performance of Mo-P /HZSM-5 catalyst" Petroleum Refinery Engineering, pp. 42-45, 2012, English abstract attached.
(Continued)

*Primary Examiner* — Sharon Pregler
(74) *Attorney, Agent, or Firm* — Calfee, Halter & Griswold LLP

(57) ABSTRACT

A catalyst for converting hydrocarbon, a method of making the same, and a method of using the same are provided. Such a catalyst includes a zeotype microporous material, a binder material, and a metal phosphide, which can be in a range of from 0.01% to 10% by weight of a total weight of the catalyst. For example, such a catalyst can be used to convert light alkene or alkane into aromatic hydrocarbon such as benzene, toluene, xylenes, and a combination thereof. The alkene may be ethylene, propylene, butylene, or a combination thereof. The alkene may be supplied directly or from a stream converted from light alkane such as methane, ethane, propane, butane, or a combination thereof.

10 Claims, 14 Drawing Sheets

(51) Int. Cl.
*B01J 21/04* (2006.01)
*B01J 37/00* (2006.01)
*B01J 37/18* (2006.01)
*C07C 2/42* (2006.01)
*C07C 2/74* (2006.01)
*B01J 37/04* (2006.01)

(52) U.S. Cl.
CPC .......... *B01J 37/0018* (2013.01); *B01J 37/04* (2013.01); *B01J 37/18* (2013.01); *C07C 2/42* (2013.01); *C07C 2/74* (2013.01); *C07C 2521/04* (2013.01); *C07C 2527/185* (2013.01); *C07C 2529/46* (2013.01)

(58) Field of Classification Search
CPC ........ B01J 29/064; B01J 29/068; B01J 29/42; B01J 29/44; B01J 29/46; B01J 29/48; B01J 29/85; B01J 37/18; B01J 37/28; B01J 8/1836; B01J 8/26
See application file for complete search history.

(56) References Cited

U.S. PATENT DOCUMENTS

2005/0227853 A1* 10/2005 Kumar .................. C10G 11/02
  502/64
2017/0305812 A1* 10/2017 Keusenkothen ......... B01J 29/48
2018/0194701 A1    7/2018 Hong

OTHER PUBLICATIONS

Ren et al., "Recent research progress of transition metal phosphide catalysts" Petrochemical Technology Application, vol. 33, No. 2. Mar. 2015, pp. 172-179, English abstract attached.

* cited by examiner

CATALYST FOR CONVERTING LIGHT OLEFIN TO AROMATICS, METHOD OF MAKING AND METHOD OF USING THE SAME

FIELD OF THE INVENTION

The disclosure relates to petrochemical processing generally. More particularly, the disclosed subject matter relates to a catalyst and a method for making aromatic hydrocarbons from light alkanes and/or alkenes; and a method of making the catalyst.

BACKGROUND

Since mid-2000, the shale gas revolution has resulted in an exponential growth in productions of natural gas (NG) and natural gas liquid (NGL) in North America. This has driven the price of NGL components, mainly ethane, to historical lows in the last several years. The low-priced and abundant ethane is the main driving force for ethylene production shifting from traditional naphtha feedstock to ethane cracker. The continuously increasing supply of both ethane and ethylene has kept them both relatively cheap and readily available in the U.S. market. Meanwhile, switching from naphtha to ethane cracker has resulted in much lower aromatics yield, causing a shortage of aromatics production, thus forming a big price gap between ethane or ethylene and aromatics.

The conversion of light hydrocarbons to aromatics is important because it provides a route for producing high value aromatic hydrocarbons, such as benzene, toluene and xylenes (BTX), from less expensive feedstock such as methane. Providing aromatics from relatively inexpensive feedstock is an economically attractive way to produce raw materials. Benzene, toluene, and xylene are very important petrochemical raw materials for polymer and other petrochemical syntheses. For example, BTX can be used as precursors for styrene monomer and other derivatives for synthesis.

The process by which light alkanes are converted into aromatic products is a catalytic aromatization reaction, which is a complex reaction that can include the steps of dehydrogenation, oligomerization, and aromatization.

EP 0785178 B1 describes a method for converting light hydrocarbon feedstock comprising at least one member selected from the group consisting of olefins and paraffins to a fixed-bed, adiabatic reactor containing a fixed catalyst bed made of a zeolite catalyst. The light hydrocarbon feedstock contact with the catalyst to produce an aromatic hydrocarbon product stream. This process requires a stream including primarily C5 olefins in order for the process to generate on-demand aromatic hydrocarbons.

Conversion of light alkane such as ethane to aromatic hydrocarbons are reported in U.S. Pat. Nos. 8,772,563; 8,946,107; U.S. Patent Application Publication No. 2017/0305812; and U.S. Patent Application Publication No. 2018/0194701. The existing catalysts and the processes used face challenges and problems. For example, rapid deactivation of the catalysts requires repeated chemical treatment and/or regeneration, which imposes higher requirements on the equipment and facility. The rapid deactivation of the catalysts also requires the use of more complex reactors, thereby increasing the operating cost.

SUMMARY

The present disclosure provides a catalyst, and a method of making and a method of using the catalyst. The catalyst is for converting hydrocarbon, for example, for converting alkene and/or alkane into aromatics.

In accordance with some embodiments, the catalyst comprises a zeotype material being microporous, a binder, which is in a range of from 0% to 50% by weight of a total weight of the catalyst, and a metal phosphide, which is in a range of from 0.01% to 10% by weight of a total weight of the catalyst.

In some embodiments, the catalyst is configured to convert an olefin-containing hydrocarbon comprising at least one alkene into an aromatic hydrocarbon. Examples of a suitable aromatic hydrocarbon include, but are not limited to, benzene, toluene, xylenes, and a combination thereof. In some embodiments, the aromatic hydrocarbon includes benzene, toluene, and xylenes (BTX). Examples of a suitable alkene include, but are not limited to ethylene, propylene, butylene, and a combination thereof.

The zeotype material is described herein. Examples of a suitable zeotype material such as a molecular sieve include, but are not limited to, alumino-silicate zeolite, an aluminophosphate (ALPO) molecular sieve, a silico-alumino-phosphate (SAPO) molecular sieve, a metallo-alumino-phosphate (MeAPO) molecular sieve, and a combination thereof. The zeotype material has a framework selected from MFI, MTW, MEL, TON, TUN, IMF, BEA, FAU, MOR, AEI, CHA, AFI, MWW, MTT, LTL, FER, EMT, and a combination thereof. Preferably, the zeotype material is ZSM-5 zeolite having a silica to alumina ratio (SAR) in a range of from 20 to 100 in some embodiments.

The binder material is described herein. Examples of suitable binder material include, but are not limited to, silica, alumina, alumina-silica, zirconia, titania, aluminum phosphate, and a combination thereof.

In some embodiments, binder is in a range of from 0% to 50% by weight of the total weight of the catalyst.

The metal phosphide is a phosphide of a metal. Examples of a suitable metal include, but are not limited to Ni, Co, Ga, Fe, Zn, Cu, Mn, In, Sn, Mo, and a combination thereof. In some embodiments, the metal phosphide is nickel phosphide or iron phosphide.

In some embodiments, the metal phosphide has an atomic or molar ratio of metal to phosphorus in a range of from 3 to 0.5, for example, from 2.5 to 1.0, from 2.5 to 0.5, from 1.5 to 0.5, or about 1. In some embodiments, metal phosphide is in a range of from 0.1% to 1% by weight of the total weight of the catalyst.

In another aspect, the present disclosure provides a method for making a catalyst. Such a method comprises a step of reducing a mixture comprising a zeotype microporous material, a binder material, and a precursor such as a metal hydrogen phosphate or metal phosphate so as to produce the catalyst as described above. The catalyst comprises of a zeotype material, a binder material in the range from 0% to 50% by weight of a total weight of the catalyst, and a metal phosphide in a range from 0.01% to 10% by weight of a total weight of the catalyst.

In some embodiments, the method further comprises steps of mixing a metal salt and phosphoric acid with a pH modification media to provide the metal hydrogen phosphate or metal phosphate, and mixing metal hydrogen phosphate or metal phosphate with the zeotype material to provide the mixture comprising the zeotype material and the metal hydrogen phosphate or metal phosphate. Examples of the zeotype material are described above. The metal phosphide is a phosphide of a metal selected from Ni, Co, Ga, Fe, Zn, Cu, Mn, In, Sn, Mo, and a combination thereof. In some embodiments, the mixture is reduced in hydrogen at an elevated temperature.

In another aspect, the present disclosure also provides a method of using a catalyst for converting hydrocarbon. In accordance with some embodiments, such a method comprises a step of converting light alkene or alkane into aromatics using the catalyst at an elevated temperature. The catalyst comprises a zeotype material being microporous, a binder in a range of from 0% to 50% by weight of a total weight of the catalyst, and a metal phosphide in a range of from 0.01% to 10% by weight of a total weight of the catalyst.

The light alkene or alkane includes an olefin-containing hydrocarbon comprising at least one alkene, which is converted into an aromatic hydrocarbon selected from the group consisting of benzene, toluene, xylenes (BTX), and a combination thereof. The at least one alkene is selected from the group consisting of ethylene, propylene, butylene, and a combination thereof. The alkene can be supplied directly or is converted from light alkane in a cracking unit in a two-step process. In some embodiments, the light alkane is ethane, and the at least one alkene comprises ethylene, which is converted from ethane.

The zeotype material and the metal phosphide are described above. For example, the metal phosphide is a phosphide of a metal selected from Ni, Co, Ga, Fe, Zn, Cu, Mn, In, Sn, Mo, and a combination thereof, and the metal phosphide has an atomic or molar ratio of metal to phosphorus in a range of from 3 to 0.5.

With the catalyst or a system including the catalyst described herein, the method provided in the present disclosure can be used to aromatize alkanes and/or alkenes with high selectivity in providing an aromatic hydrocarbon such as one or more BTX products. The resulting BTX yield is high and the catalyst has a good lifetime during use.

BRIEF DESCRIPTION OF THE DRAWINGS

The present disclosure is best understood from the following detailed description when read in conjunction with the accompanying drawings. It is emphasized that, according to common practice, the various features of the drawings are not necessarily to scale. On the contrary, the dimensions of the various features are arbitrarily expanded or reduced for clarity. Like reference numerals denote like features throughout specification and drawings.

DETAILED DESCRIPTION

This description of the exemplary embodiments is intended to be read in connection with the accompanying drawings, which are to be considered part of the entire written description.

For purposes of the description hereinafter, it is to be understood that the embodiments described below may assume alternative variations and embodiments. It is also to be understood that the specific articles, compositions, and/or processes described herein are exemplary and should not be considered as limiting.

In the present disclosure the singular forms "a," "an," and "the" include the plural reference, and reference to a particular numerical value includes at least that particular value, unless the context clearly indicates otherwise. Thus, for example, a reference to "a reactor" or "a hydrocarbon" is a reference to one or more of such structures and equivalents thereof known to those skilled in the art, and so forth. When values are expressed as approximations, by use of the antecedent "about," it will be understood that the particular value forms another embodiment. As used herein, "about X" (where X is a numerical value) preferably refers to ±10% of the recited value, inclusive. For example, the phrase "about 8" preferably refers to a value of 7.2 to 8.8, inclusive; as another example, the phrase "about 8%" preferably (but not always) refers to a value of 7.2% to 8.8%, inclusive. Where present, all ranges are inclusive and combinable. For example, when a range of "1 to 5" is recited, the recited range should be construed as including ranges "1 to 4", "1 to 3", "1-2", "1-2 & 4-5", "1-3 & 5", "2-5", and the like. In addition, when a list of alternatives is positively provided, such listing can be interpreted to mean that any of the alternatives may be excluded, e.g., by a negative limitation in the claims. For example, when a range of "1 to 5" is recited, the recited range may be construed as including situations whereby any of 1, 2, 3, 4, or 5 are negatively excluded; thus, a recitation of "1 to 5" may be construed as "1 and 3-5, but not 2", or simply "wherein 2 is not included." It is intended that any component, element, attribute, or step that is positively recited herein may be explicitly excluded in the claims, whether such components, elements, attributes, or steps are listed as alternatives or whether they are recited in isolation.

Due to the abundant availability of ethane, direct conversion of light alkanes to aromatics has been a major interest for academia and industry. Over the past two decades, companies have applied or are currently applying for patents worldwide related to technologies of converting light alkanes to aromatics.

Figure 1:
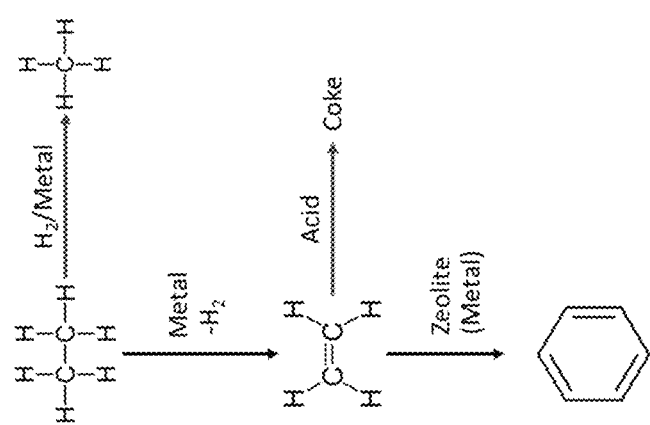
FIG. 1 illustrates simplified reaction schemes from ethane to aromatics in some embodiments.

The mechanism of the reactions is depicted in a simplified scheme in FIG. 1. A bifunctional catalyst is generally required, and a noble metal, such as Pt or Pd, is combined with ZSM-5 zeolite for the catalyst in some embodiments. Due to thermodynamic limitations, high temperature is required for alkane dehydrogenation, while mid-range temperature is optimal for olefin aromatization due to its exothermic reaction. Under optimized conditions, a typical BTX yield per pass is between 30-40%.

U.S. Pat. No. 8,946,107 discloses a process for the conversion of ethane to aromatic hydrocarbons, with results shown in its Table 1. The reaction conditions include 630° C. and a gas hourly space velocity (GHSV) is 1,000 (i.e., 15 L/hr) on a Pt—Fe/ZSM-5 catalyst. The initial ethane conversions were 50-60% with a total aromatics selectivity of 53-66%. However, the catalyst quickly loses activity to less than 40%. This is possibly due to coke formation deactivating the catalyst at such high reaction temperatures. Coke can be removed during regeneration every few hours; however, the high reaction temperature and frequent regeneration also cause noble metal nanoparticles to sinter. In addition to the undesired frequent regeneration and activity loss, the catalyst also shows methane selectivity reach as high as 41%. As a by-product, methane is a low value chemical, resulting in inefficient use of the ethane feed.

Direct conversion of ethane to aromatics requires high temperatures for alkane dehydrogenation and mid-range temperatures for alkene aromatization. This causes major drawbacks such as (1) limited ethane conversion due to temperature limit, (2) fast catalyst deactivation caused by coking where frequent catalyst regeneration is required, (3) high cracking/hydrolysis production of methane, (4) high portion of heavies component, such as naphthalene, in liquid product, and (5) noble metal, such as Pt or Pd, required in the catalyst formulation specifically for alkane dehydrogenation. These shortcomings limit existing one-step processes of ethane aromatization from being economically feasible or producing high aromatics yields.

On the other hand, with the current trend in oil industry shifting from fuel to chemical production, aromatic compounds are more attractive products compared to fuel.

Light alkanes such as ethane are mainly used as feed stock to produce olefins in some embodiments. One of the key processes is steam cracking. Steam cracking is a petrochemical process, in which saturated hydrocarbons such as naphtha are broken down into smaller, often unsaturated, hydrocarbons. It is the principal industrial method for producing the lighter alkenes such as ethylene and propylene. Aromatics can also be recovered from steam cracking, which accounts for ⅓ of total aromatics production worldwide. When ethane is used as the only feedstock in some embodiments, aromatics yield drops to near zero, which breaks the balance within chemical industry.

Because of the relatively inexpensive price of ethane and ethylene and the readily available feedstock, it is desirable to have aromatization of alkanes or alkenes to produce light aromatics (e.g., BTX). For example, compared to C5 olefins, lower alkanes such as ethane can be a much more cost-effective feedstock for aromatics production.

The present disclosure provides a catalyst and a process for producing aromatics such as benzene, toluene, and xylenes (BTX) comprising aromatization of alkanes and/or alkenes. In accordance with some embodiments, a type of catalyst is provided for converting light alkenes to aromatics and other liquid fuel with high hydrocarbon yields, such as benzene, toluene, xylenes, and other liquid yields. The catalyst also slows deactivation and provides regenerability.

In some embodiments, the catalyst provided in the present disclosure is used in a two-step process for low alkanes to liquid conversion, offering an alternative catalyst synthesis for this process. This alternative catalyst contains metal phosphide modifications on the zeolite that results in high aromatic product yields, long catalyst lifetime, and good long-term stability. A two-step process is preferred in some embodiments. The catalyst described herein is used in the second step involving converting light alkene or olefin to aromatics.

Unless expressly indicated otherwise, the term "zeotype" used herein is understood to encompass a microporous material such as molecular sieve including, but not limited to an alumino-silicate zeolite, an alumino-phosphate (ALPO) molecular sieve, a silico-alumino-phosphate (SAPO) molecular sieve, a metallo-alumino-phosphate (MeAPO) molecular sieve, and a combination thereof. The zeotype material may have a framework selected from MFI MTW, MEL, TON, TUN, IMF, BEA, FAU, MOR, AEI, CHA, AFI, MWW, MTT, LTL, FER, and EMT. A zeotype material may include zeolite. Zeolite and zeotype materials have micropores having a size from a few angstrom to 2 nanometers, and are considered as microporous. Zeolites are crystalline microporous aluminosilicate materials comprising Al and Si, and zeolite structures have been classified and organized by the International Zeolite Association. An acronym with three letters is used to describe the framework type. Zeotype materials have a broader scope and include materials having similar structure to zeolite without necessarily having Al and/or Si. For example, $AlPO_4$ materials, which have no Si but have the same topology of zeolite, are zeotype materials.

Unless expressly indicated otherwise, the structural units such as reactors for cracking or aromatization processes are fluidly coupled together as shown. The term "fluidly coupled" or "fluidly connected" is understood to mean that the units are connected with pipes, valves and related structures so that gas or liquid stream can flow from one unit to another unit. The system having the units can be operated continuously with the steps performed concurrently, or in a batch process.

Unless expressly indicated otherwise, the percentages (%) described herein are by weight. The composition and the method provided in the present disclosure may also be applicable if the percentages are by volume or by moles.

Unless expressly indicated otherwise, the term "light alkane" described herein is understood to encompass one or more alkanes having one to four carbons. For example, such a light alkane is selected from the group consisting of methane, ethane, propane, butane, and a combination thereof. In some embodiments, ethane is used as the feedstock of light alkane.

Similarly, the term "light alkene" or "light olefin" described herein is understood to encompass one or more alkanes having two to four carbons. For example, such a light alkene is selected from the group consisting of ethylene, propylene, butylene, and a combination thereof. In some embodiments, "light alkene" is ethylene. The catalyst described herein may also be used for converting hydrocarbon having five or more than five carbon atoms.

Unless expressly indicated otherwise, the term "an aromatic hydrocarbon" described herein is understood to encompass one or more aromatic hydrocarbons. For example, such an aromatic hydrocarbon is selected from the group consisting of benzene, toluene, xylenes, and a combination thereof. Xylenes include different xylenes having different locations of substitution. A resulting product may be benzene, toluene, xylenes, or a combination thereof. In some embodiments, the resulting product includes benzene, toluene, and xylenes (BTX).

Unless expressly indicated otherwise, the term "metal phosphide" used herein is understood to encompass monophosphide, polyphosphide, and a combination thereof. For example, nickel phosphide may include eight mono- and polyphosphides of nickel such as $Ni_3P$, $Ni_5P_2$, $Ni_{12}P_5$, $Ni_2P$, $Ni_5P_4$, $NiP$, $NiP_2$, $NiP_3$, and a combination thereof. In some embodiments, nickel phosphide comprises NiP, iron phosphide may comprise FeP.

The present disclosure provides a catalyst, a method of making and a method of using the catalyst. The catalyst is for converting hydrocarbon, for example, for converting alkene or alkane into aromatics.

In accordance with some embodiments, the catalyst comprises a zeotype material being microporous, a binder in a range of from 0% to 50% by weight of a total weight of the catalyst, and a metal phosphide, which is in a range of from 0.01% to 10% by weight of a total weight of the catalyst.

In some embodiments, the catalyst is configured to convert an olefin-containing hydrocarbon comprising at least one alkene into an aromatic hydrocarbon. Examples of a suitable aromatic hydrocarbon include, but are limited to, benzene, toluene, xylenes, and a combination thereof. In some embodiments, the aromatic hydrocarbon includes benzene, toluene, and xylenes (BTX). Examples of a suitable alkene include, but are not limited to ethylene, propylene, butylene, and a combination thereof.

The zeotype material is described herein. Examples of a suitable zeotype material such as a molecular sieve include, but are not limited to, alumino-silicate zeolite, an alumino-phosphate (ALPO) molecular sieve, a silico-alumino-phosphate (SAPO) molecular sieve, a metallo-alumino-phosphate (MeAPO) molecular sieve, and a combination thereof. The zeotype material has a framework selected from MFI, MTW, MEL, TON, TUN, IMF, BEA, FAU, MOR, AEI, CHA, AFI, MWW, MTT, LTL, FER, EMT, and a combination thereof. Preferably, the zeotype material is ZSM-5 zeolite having a silica to alumina ratio (SAR) in a range of from 20 to 100 in some embodiments. ZSM-5 zeolite has a framework of MFI.

Suitable binder materials include silica, alumina, alumina-silica, zirconia, titania, aluminum-phosphate, and a combination thereof. The binder may be optional in some embodiments. The binder might be in a range of from 0% to 50% by weight, for example, 0.1-50%, of a total weight of the catalyst. The suitable content might in any suitable range, for example, 1-40%, 1-30%, 1-20%, or 1-10%

The metal phosphide is a phosphide of a metal. Examples of a suitable metal include, but are not limited to, Ni, Co, Ga, Fe, Zn, Cu, Mn, In, Sn, Mo, and a combination thereof. In some embodiments, the metal phosphide is nickel phosphide, iron phosphide, or a combination thereof.

In some embodiments, the metal phosphide has a ratio of metal to phosphorus in a range of from 3 to 0.5, for example, from 2.5 to 1.0, from 2.5 to 0.5, from 1.5 to 0.5, or about 1. In some embodiments, metal phosphide is in a range of from 0.1% to 1%, from 0.1% to 2%, or from 0.1% to 5%, by weight of the total weight of the catalyst.

The present disclosure also provides a method for making a catalyst. Such a method comprises a step of reducing a mixture comprising a zeotype material being microporous and a metal hydrogen phosphate or metal phosphate so as to produce the catalyst as described above. The catalyst comprises the zeotype material, a binder in a range of from 0% to 50% by weight of a total weight of the catalyst, and a metal phosphide in a range of from 0.01% to 10% by weight of a total weight of the catalyst.

In some embodiments, a metal salt and phosphoric acid are mixed with ammonia solution to provide the metal hydrogen phosphate or metal phosphate. The pH modification media may be selected from ammonium hydroxide, amine, alkaline metal hydroxide, alkaline earth metal hydroxide, quaternary ammonium hydroxide, alkaline metal carbonate, alkaline metal bicarbonate, alkaline metal acetate, urea, and a combination thereof. Metal hydrogen phosphate or metal phosphate or a mixture of both is then mixed with the zeotype material to provide the mixture comprising the zeotype material and the metal hydrogen phosphate or metal phosphate. In some other embodiments, a zeotype material can be also mixed with metal phosphide or precursors directly.

In some embodiments, a binder can be added before, during, or after zeotype material mixing with metal phosphide or metal-phosphate.

The mixture containing precursors such as metal hydrogen phosphate or metal phosphate or both can be reduced in hydrogen at an elevated temperature. The temperature can be in any suitable range, for example, in a range of from 400° C. to 800° C. (e.g., 500-650° C.) for a period of time. The period of time can be any suitable length of time, for example, from 30 minutes to 3 hours (e.g., 30 minutes to 2 hours).

Examples of the zeotype material are described above. The metal phosphide is a phosphide of a metal selected from Ni, Co, Ga, Fe, Zn, Cu, Mn, In, Sn, Mo, and a combination thereof. In some embodiments, Ni and Fe are used.

The present disclosure also provides a method of using the catalyst as described for converting hydrocarbon. In accordance with some embodiments, such a method comprises a step of converting light alkene or alkane into aromatics using the catalyst at an elevated temperature. The temperature can be in any suitable range, for example, in a range of from 300° C. to 800° C. (e.g., 500-650° C. or 550-650° C.) for a period of time. Other reaction conditions include a pressure and a gas hourly space velocity (GHSV). The pressure may be in any suitable range, for example, from 0.5 bar to 20 bar (e.g., 0.5-2 bar). The GHSV may be in a range of from 500 $mL_C/g_{cat}*hr$ to 10,000 $mL_C/g_{cat}*hr$.

The light alkene or alkane includes an olefin-containing hydrocarbon comprising at least one alkene, which is converted into an aromatic hydrocarbon selected from the group consisting of benzene, toluene, xylenes (BTX), and a combination thereof. The at least one alkene is selected from the group consisting of ethylene, propylene, butylene, and a combination thereof. The alkene can be supplied directly or is converted from light alkane in a cracking unit in a two-step process. In some embodiments, the light alkane is ethane, and the at least one alkene comprises ethylene, which is converted from ethane.

For example, the light olefin may be from a cracker unit, in which light alkane is converted to a product stream containing alkene. The conversion of from alkene to aromatics can be performed in an aromatization reactor using the catalyst as described herein.

The catalyst provided in the present disclosure have many advantages. For example, compared to a one-step catalyst, where Pt is normally used, which is costly and easily sintered, the catalyst or the catalyst system provided in the present disclosure requires no noble metal. The catalyst is also regenerable with proven good long-term stability and high yields. Compared to metal-free ZSM-5 (pure ZSM-5), the metal phosphide modified ZSM-5 produces higher BTX product yield, longer catalyst lifetime, and better long-term stability at lower temperatures. The catalyst also maintains excellent performance with increased GHSV and pressure and maintain good performance with relatively low weight-loading.

The catalysts provided in the present disclosure may be used for a process for converting hydrocarbon including, but not limited to, aromatization, hydrodesulfurization, hydrodeoxygenation, dehydrogenation, oligomerization, alkylation, dealkylation, isomerization, and hydrocracking.

EXPERIMENTAL

The implementation of the invention involves: 1. Synthesis of metal phosphide or precursor; 2. Modification of zeolite with metal phosphide or precursor; and 3. Activation of catalyst. Alternatively, metal phosphide or precursor might be prepared in-situ during zeolite modification step. Activation step might be also omitted if metal phosphide other than precursors is used.

In the experiments described herein, the catalysts, which were a metal phosphide modified ZSM-5 at a suitable loading such as 1 wt. % loading were synthesized. The catalysts were prepared via physical mixture were used. For a general procedure of catalyst synthesis, the ZSM-5 powder with 30 silica-to-alumina ratio (SAR) was mixed with metal phosphide or precursor to make a catalyst. The catalyst of a 20-40 mesh size was tested.

The chemicals used include: tetraammineplatinum (Pt, II) nitrate, ≥50.0% Pt basis, available from Sigma-Aldrich; Nickel (Ni, II) nitrate hexahydrate, purum p.a. crystallized, ≥97.0%, available from Sigma-Aldrich; Iron (Fe, III) nitrate nonahydrate, ACS Reagent, ≥98%, available from Sigma-Aldrich; Ammonium nitrate, ACS Reagent, ≥98%, available from Sigma-Aldrich; Ammonium hydroxide solution, ACS Reagent, 28.0-30.0% $NH_3$ basis, available from Sigma-Aldrich; and Zeolite (ZSM-5) having 30 SAR (silica to alumina ratio), CBV 3024, available from Zeolyst.

The characterization for elemental ratio is performed on an energy dispersive x-ray fluorescence (XRF) spectrometer (model: Shimadzu EDX-7000).

In the evaluating test of a catalyst, the catalyst was loaded in a ½" quartz or alumina reactor. The reaction temperature ranged from 500-650° C., preferably at 550° C. The reaction pressure ranged from ambient pressure up to 5 bar. The feed gases were set to mimic the composition of effluent from an ethane cracker, with a mixed gas feed volume ratio of $C_2H_6$, $C_2H_4$, $H_2$ and $N_2$ in a ratio of 0.67:1:1:1. $N_2$ was used as an internal standard for analysis. All the products were analyzed using gas chromatography (GC) with a system made by Agilent Technologies.

The activation of a metal phosphide containing catalyst is performed through reduction in $H_2$ as described herein. The regeneration of a deactivated metal phosphide containing catalyst is performed through burning in $O_2$ and reduction in $H_2$. A catalyst is deemed as inactive when the product yield is low. The experiment may be stopped for in-situ regeneration of the catalyst, in which the system is purged with nitrogen gas at 550° C. for a length of time, a gas mixture of 10% $O_2$ in $N_2$ is used to regenerate the catalyst at 550° C. for 4 hours. Another $N_2$ purge is performed before the catalyst undergoes another round of $H_2$ reduction before testing.

Example 1

A molar ratio of 0.4:1 of nickel nitrate ($Ni(NO_3)_2$) and phosphoric acid ($H_3PO_4$) were mixed. Ammonium hydroxide was added until pH of the mixture was greater than 7. The mixture was filtered via vacuum while being thoroughly washes with deionized (DI) water. The precipitated sample, once dried in oven at 80° C. overnight, was designated as Sample A, with a mole ratio of Ni:P of 1:1 and having a formula of $NiHPO_4$. Synthesis of Sample A is shown in Scheme 1 as follows:

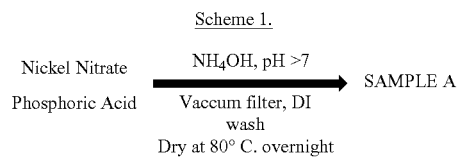

Scheme 1.

Example 2

0.1 g of Sample A and 10 g of 30 SAR ZSM-5 were thoroughly mixed. The mixed powder was pressed using a hydraulic press and calcined at 550° C. for 4 hours in air. Once meshed and sieved to 20-40 mesh, the sample was designated as Sample B with nominal weight loading of 0.18% nickel hydrogen phosphate and a nominal ratio of 1:1 Ni:P. Synthesis of Sample B is shown in Scheme 2 as follows:

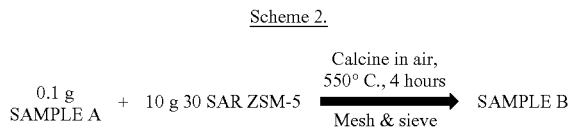

Scheme 2.

Example 3

Sample B was reduced in hydrogen at 630° C. for 60 minutes as shown in Scheme 3. The reduced sample is designated as Sample C, which comprises nickel phosphide (NiP) and zeolite. Sample C can be also directly made from nickel phosphide and zeolite.

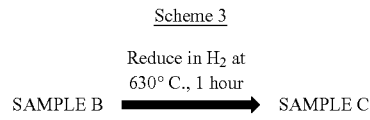

Scheme 3

Example 4

0.5 g of Sample A was thoroughly mixed with 10 g of 30 SAR ZSM-5. The mixed powder was pressed using a hydraulic press and calcine at 550° C. for 4 hours in air. Once meshed and sieved to 20-40 mesh, the sample is designated as Sample D with nominal weight loading of 1.33% nickel hydrogen phosphate and a nominal ratio of 1:1 Ni:P. Sample D was reduced in $H_2$ at 630° C. for 60 minutes in $H_2$. The reduced sample is designated at Sample E, which comprises nickel phosphide. Syntheses of Sample D and Sample E are shown in Schemes 4a and 4b, respectively, as follows:

Syntheses of Samples F, G, and H are shown in Schemes 5a, 5b, and 5c, respectively, as follows:

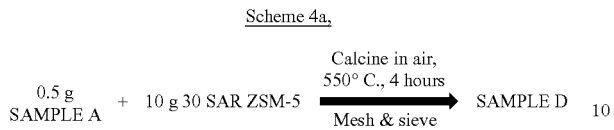

Scheme 4a.

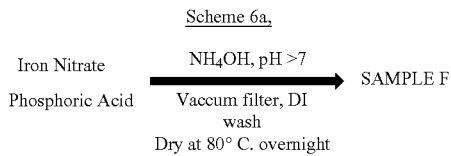

Scheme 6a.

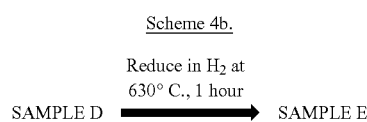

Scheme 4b.

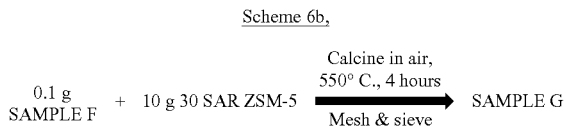

Scheme 6b.

Example 5

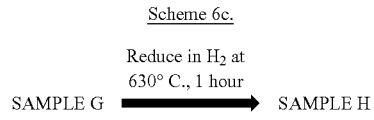

Scheme 6c.

0.1 g of Nickel Phosphide was thoroughly mixed with 8 g of 30 SAR ZSM-5 and 2.6 g of pseudo-boehmite as binder and water. This mixture was extruded and dried at room temperature overnight. After calcination at 550° C. for 4 hours and meshed and sieved to 20-40 mesh, the sample was then designated as Sample O with 0.55% nickel phosphide. The nickel phosphide sample was obtained from Sigma Aldrich. Synthesis of Sample O is shown in Scheme 5:

Example 7

0.5 g of Sample F was thoroughly mixed with 10 g of 30 SAR ZSM-5. The mixed powder was pressed using a hydraulic press and calcined at 550° C. for 4 hours in air. Once meshed and sieved to 20-40 mesh, the sample was designated as Sample I with nominal weight loading of 0.96% iron hydrogen phosphate) and a nominal ratio of 2:3 Fe:P. Sample I was reduced in $H_2$ at 630° C. for 60 minutes. The reduced sample is designated at Sample J, which iron phosphide and zeolite. Syntheses of Samples I and J are shown in Schemes 6a and 6b, respectively, as follows:

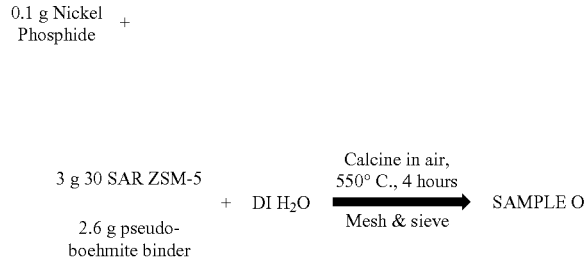

Scheme 5.

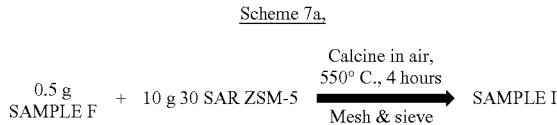

Scheme 7a.

Example 6

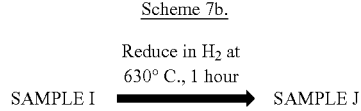

Scheme 7b.

A molar ratio of 0.3:1 of iron (III) nitrate and phosphoric acid were mixed. Ammonium hydroxide was added until pH of the mixture was greater than 7. The mixture was filtered via vacuum while being thoroughly washed with DI water. Precipitated sample, once dried in oven at 80° C. overnight, was designated as Sample F. 0.1 g of Sample F was thoroughly mixed with 10 g of 30 SAR ZSM-5. The mixed powder was pressed using a hydraulic press and calcined at 550° C. for 4 hours in air. Once meshed and sieved to 20-40 mesh, the sample was designated as Sample G with nominal weight loading of 0.19% iron hydrogen phosphate and a nominal ratio of about 2:3 Fe:P. Sample G contains iron hydrogen phosphate. Sample G was reduced in $H_2$ at 630° C. for 60 minutes, resulting in Sample H, which contains iron phosphide and zeolite.

Example 8

ZSM-5 modified with nickel hydrogen phosphate mixture in water (Sample A mixed in water) was synthesized and dried in oven at 80 C. After calcined at 550° C. for 4 hours and meshed and sieved to 20-40 mesh, the sample was then designated as Sample K as shown in Scheme 8:

Scheme 8.

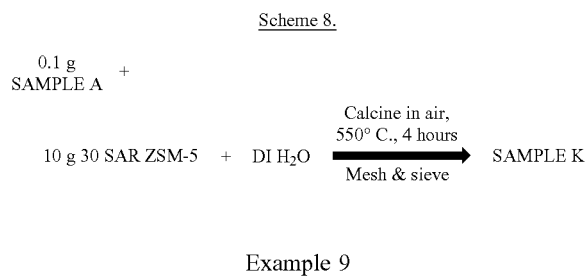

Example 9

As a comparative sample, metal-free and Pt/ZSM-5 catalysts were synthesized. ZSM-5 zeolite with 30 SAR was mixed and extruded with pseudo-boehmite as binder, nitric acid, and water. After drying and calcination in the furnace at 550° C. for 4 hours, this sample was designated as Sample L.

To synthesize a Pt-modified catalyst, a wet impregnation was completed with Sample L. The extruded sample was mixed with a solution of tetraammineplatinum nitrate and ammonium nitrate on a rotary vacuum. After dried, this catalyst was then calcined again at 550° C. for 4 hours. After reduction in hydrogen at 630° C. for 1 hour, the catalyst was designated as Sample M.

The last comparative sample was a 1% Fe/ZSM-5 catalyst. ZSM-5 zeolite with 30 SAR was mixed with Ludox (AS-40 colloidal silica) and dried and calcined in the furnace at 550° C. for 4 hours. A wet impregnation was then completed with a solution mixture of iron nitrate and ammonium nitrate. Once dried, the catalyst was then calcined again at 550° C. for 4 hours, and designated as Sample N.

Example 10

Tests were performed to compare between the 1-step and 2-step ethane aromatization reactions, in which the control Pt/ZSM-5 (Sample M) and an experimental sample NiP/ZSM-5 (Sample C) catalysts were used, respectively. For the Pt/ZSM-5 catalyst, reaction conditions were at 630° C., 1 bar, and GHSV (gas hourly space velocity) of 1000 $mL_C/g_{cat}$*hr, while the two-step reaction using the NiP/ZSM-5 catalyst (Sample C) was performed at 550° C., 1 bar, and GHSV of 2000 $mL_C/g_{cat}$*hr. Both tests had a feed gas mixture of $C_2H_6:N_2$ in a volume ratio of 1.6:1. However, the reaction with the 1-step catalyst was completed in a single reactor, converting ethane directly to BTX. The reaction with the 2-step catalyst was done via cascade-mode, converting ethane to ethylene and then ethylene to aromatics. A cascade-mode system includes two reactors in tandem where the first reactor undergoes thermal ethane dehydrogenation at 750° C. and the second undergoes ethylene aromatization at desired temperatures. The reaction/cycle time the nickel phosphide containing catalyst (Sample C) was 3825 minutes, compared to that (605 minutes) for the Pt/ZSM-5 catalyst (Sample M). All data values were calculated based on ethane.

Figure 2:
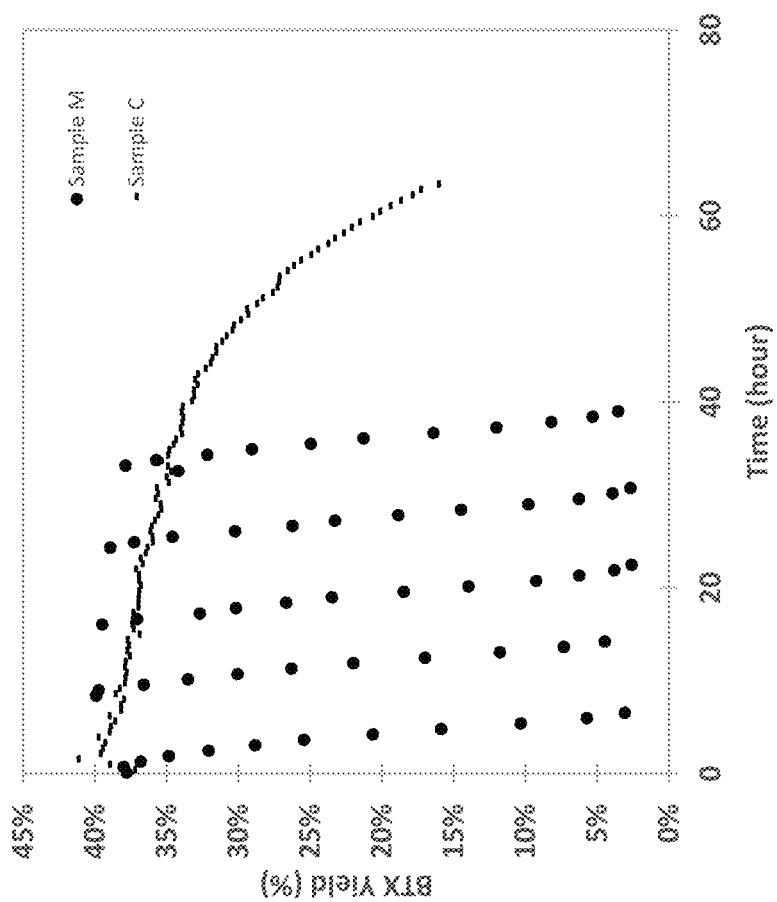
FIG. 2 shows the BTX yield for the processes of one-step ("1-step") using Pt/ZSM-5 (Sample M) and two-step ("2-step") using NiP/ZSM-5 (Sample C) in accordance with some embodiments.

FIG. 2 shows that the 2-step process with the invented catalyst (Sample C) provides a better performance, as shown in the stability and BTX yield. Sample C maintains a relatively high BTX yield (>35%) in the same amount of time the 1-step process catalyst (Sample M) completes 6 total cycles.

Example 11

Sample C as an experimental catalyst containing nickel phosphide and Sample H as an experimental catalyst containing iron phosphide were evaluated and compared to Sample L as a comparative catalyst, which is metal-free (MF). The reactions were performed at fixed temperature (550° C.), pressure (1 bar), and gas hourly space velocity (2000 $mL_C/g_{cat}$*hr), respectively. The catalysts were tested with a mixed feed of $C_2H_6:C_2H_4:H_2:N_2$ in a ratio of 0.67:1:1:1. All data values were calculated based on ethane.

Figure 3:
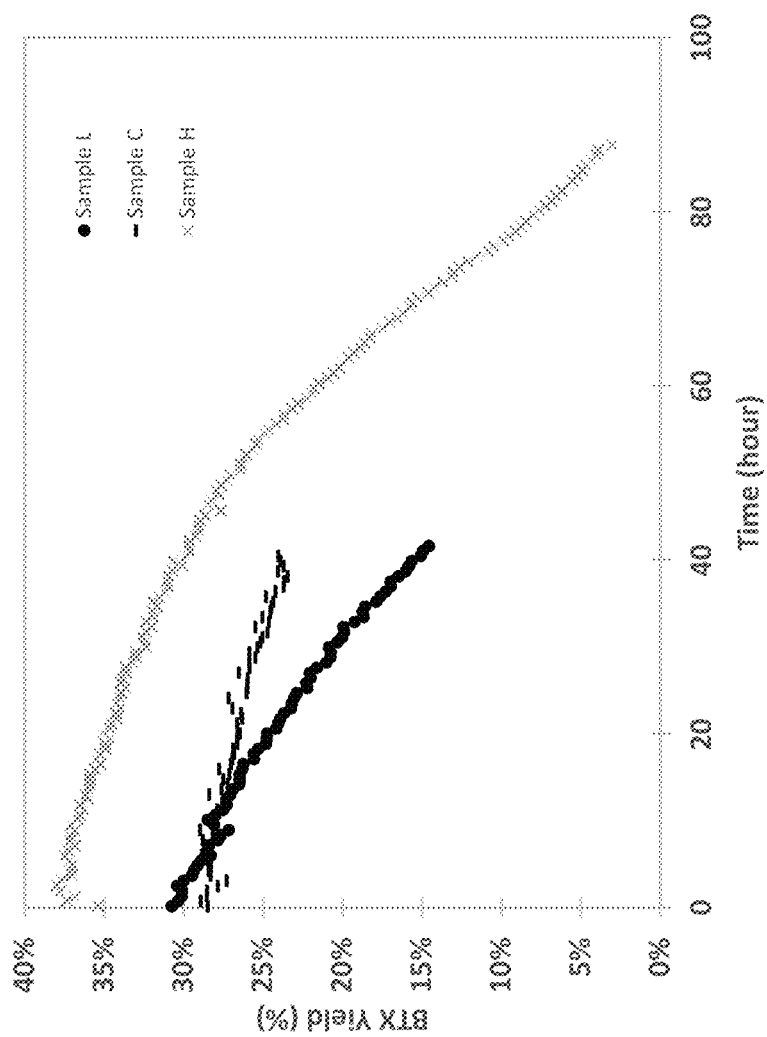
FIG. 3 shows the BTX yield change with time on stream (TOS) for nickel phosphide (Sample C), iron phosphide (Sample H), and metal-free (Sample L) at 550° C., respectively, in accordance with some embodiments.

FIG. 3 shows that the metal phosphide catalysts (Sample C and Sample H) outperforms the metal-free catalyst (Sample L) in terms of stability. The iron phosphide catalyst (Sample H) outperforms the metal-free catalyst in both yield and stability.

Example 12

At higher weight loading, the nickel phosphide catalyst (Sample E) and the iron phosphide catalyst (Sample J) were evaluated at fixed conditions of 550° C., 1 bar, GHSV of 2000 $mL_C/g_{cat}$*hr with a feed gas mixture of $C_2H_6:C_2H_4:H_2:N_2$ in a volume ratio of 0.67:1:1:1. The metal-free catalyst (Sample L) was also shown as comparison and was tested with fixed conditions of 550° C., 1 bar, GHSV of 2000 $mL_C/g_{cat}$*hr, with feed gas mixture of $C_2H_6:N_2$ in a volume ratio of 1.6:1 in a cascade mode. The cascade mode includes two reactors in tandem where the first reactor undergoes thermal ethane dehydrogenation at 750° C. and the second undergoes ethylene aromatization at desired temperatures. All data values were calculated based on ethane.

Figure 4A:
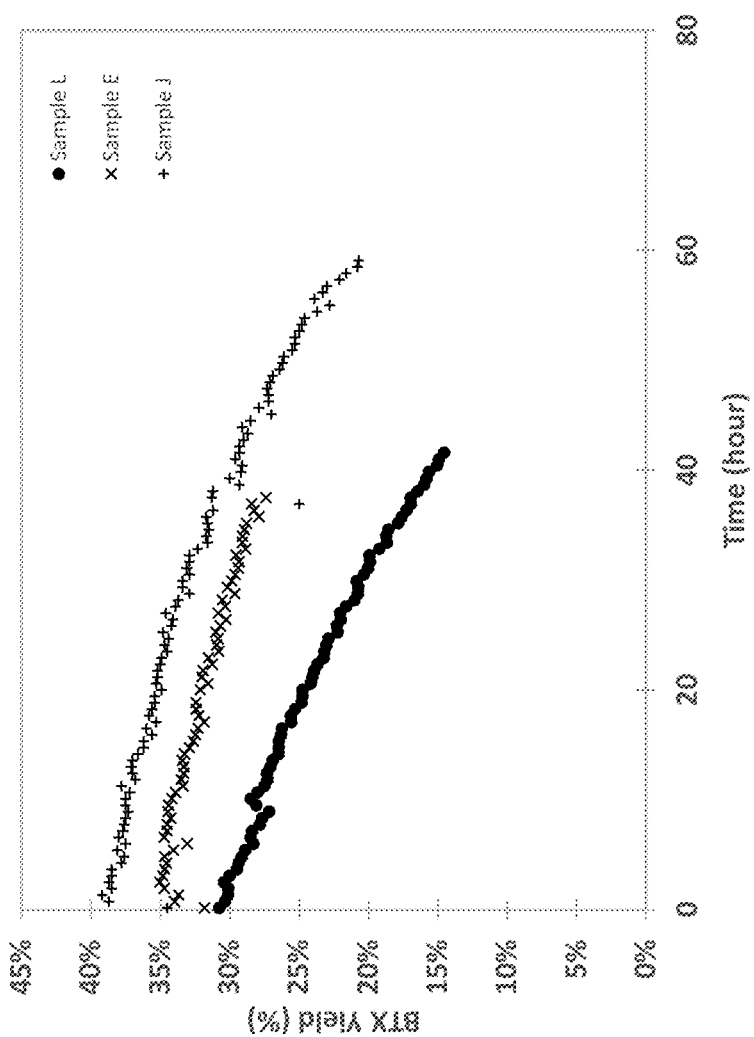
FIGS. 4A and 4B show the BTX yield over TOS and the methane selectivity over the ethylene breakthrough, respectively, for metal phosphides including NiP/ZSM-5 (Sample E) and FeP/ZSM-5 (Sample J) at various weight loadings in comparison to the metal-free (Sample L) catalyst in accordance with some embodiments.
Figure 4B:
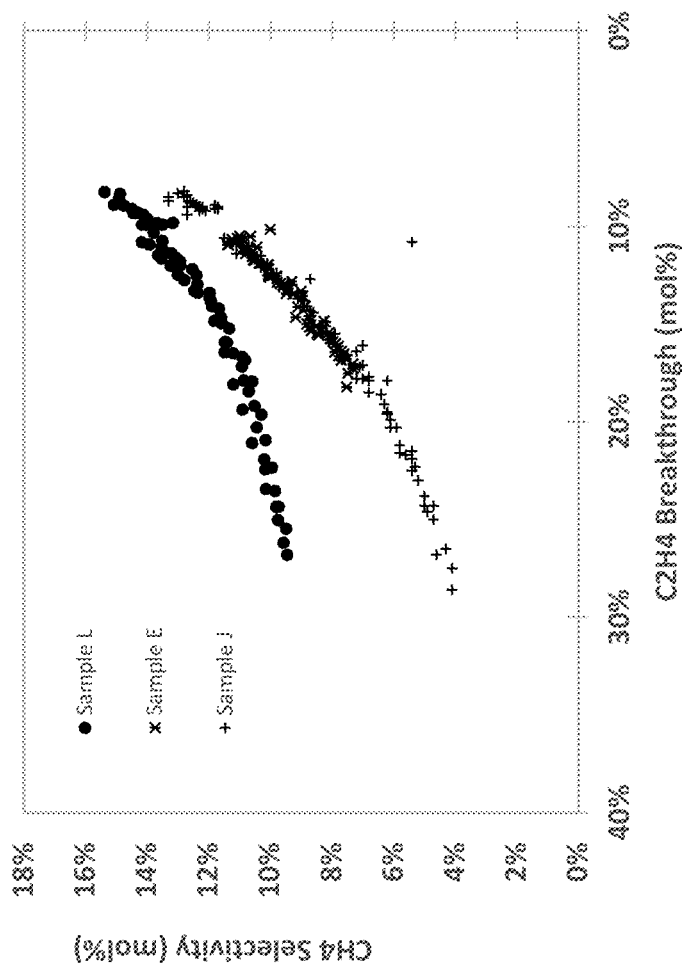

The results including product selectivity and the BTX yield are shown in FIGS. 4A-4B as an understanding of whether changes in the weight-loading of the metal phosphide catalyst would have any effect on its performance.

At a higher weight loading, for the nickel phosphide catalyst at 1.33% Ni/P (Sample E) and for the iron phosphide catalyst at 0.96% Fe/P (Sample J), both metal phosphide catalysts outperform the metal-free catalyst (Sample L) in both BTX yield and stability.

This observation can further be explained in FIG. 4B, which showing the $CH_4$ selectivity over $C_2H_4$ breakthrough, which gives a good indication of the reaction mechanism. A lower $C_2H_4$ breakthrough may indicate more $C_2H_4$ feed has been converted, either to $CH_4$ or more aromatics. As seen from Sample E and J, FIG. 4B indicates that the metal phosphide catalysts converts more of the feed to BTX further supporting the data seen in FIG. 4A. In comparison, the metal free catalyst (Sample L) has a higher $CH_4$ selectivity for any given $C_2H_4$ breakthrough value, indicating that the addition of metal phosphide more effectively converts the feed to BTX.

Example 13

The effects of an iron-only catalyst (1% Fe, Sample N) and the iron phosphide containing catalyst (Sample H, J) were evaluated for the ethylene aromatization reaction. Tests were conducted at 550° C., 1 bar, and GHSV of 2000 $mL_C/g_{cat}$*hr with a feed gas mixture of $C_2H_6:C_2H_4:H_2:N_2$ in a volume ratio of 0.67:1:1:1 for Sample H and J, while the iron-only catalyst was tested via a cascade mode at 400° C., 1 bar, and GHSV of 2000 $mL_C/g_{cat}$*hr with a feed gas mixture of $C_2H_6:N_2$ in a volume ratio of 1.6:1. The cascade mode includes two reactors in tandem where the first reactor undergoes thermal ethane dehydrogenation at 750° C. and the second undergoes ethylene aromatization at desired temperatures. All data values were calculated based on ethane.

Figure 5A:
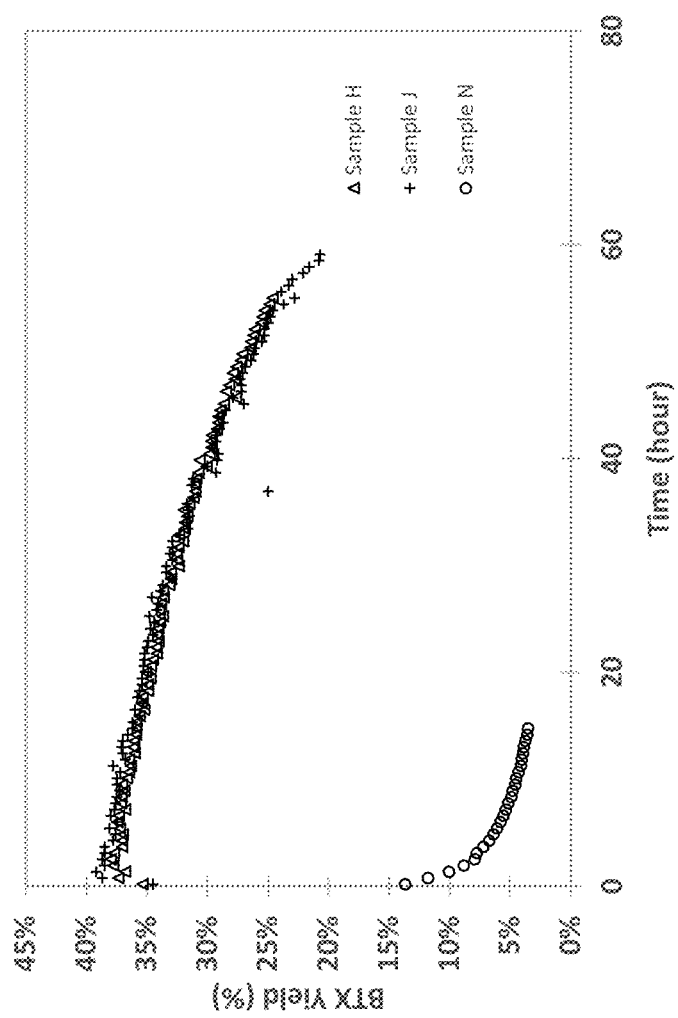
FIGS. 5A and 5B show the BTX yield and ethylene breakthrough over TOS, respectively, for iron phosphide catalysts (0.1% FeP/ZSM-5, Sample H, and 1% FeP/ZSM-5, Sample J) in comparison with 1% Fe (Sample N) in accordance with some embodiments.
Figure 5B:
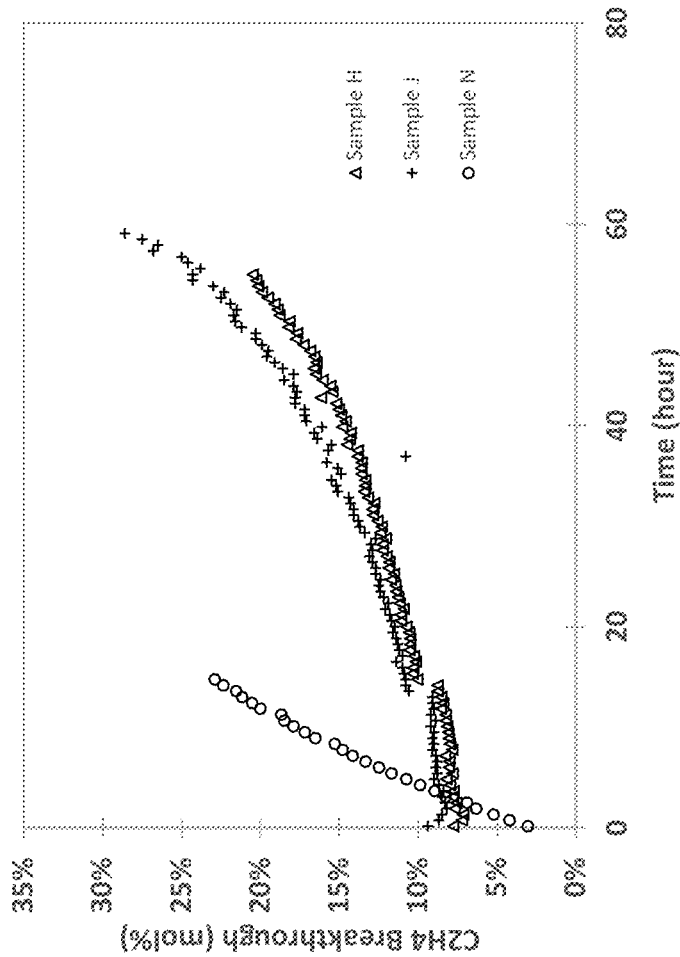

FIG. 5A shows the significant benefit of the addition of phosphide to the iron catalyst. The iron-only catalyst, Sample N, exhibits essentially no BTX yield, not reaching 15% initially with a steady decline over time. On the other hand, with iron phosphide (Sample H, J) increased BTX yield as well as catalyst lifetime. FIG. 5B shows the $C_2H_4$ breakthrough over time. A lower $C_2H_4$ breakthrough indicates more efficient conversion of the feed to BTX.

Example 14

To understand the capability of the metal phosphide catalysts, the effect of pressure on BTX and byproducts were investigated using a nickel phosphide containing catalyst (Sample C) with comparison to a metal-free catalyst (Sample L). The results for single cycle lifetime were obtained at pressure of 1 bar and 5 bar, fixed temperature of 550° C., and GHSV of 2000 $mL_C/g_{cat}$*hr. All tests were with a gas mixture of $C_2H_6:C_2H_4:H_2:N_2$ in a volume ratio of 0.67:1:1:1. The test with the metal-free catalyst at 5 bar was performed with GHSV of 4000 $mL_C/g_{cat}$*hr. All data values were calculated based on ethane.

Figure 6A:
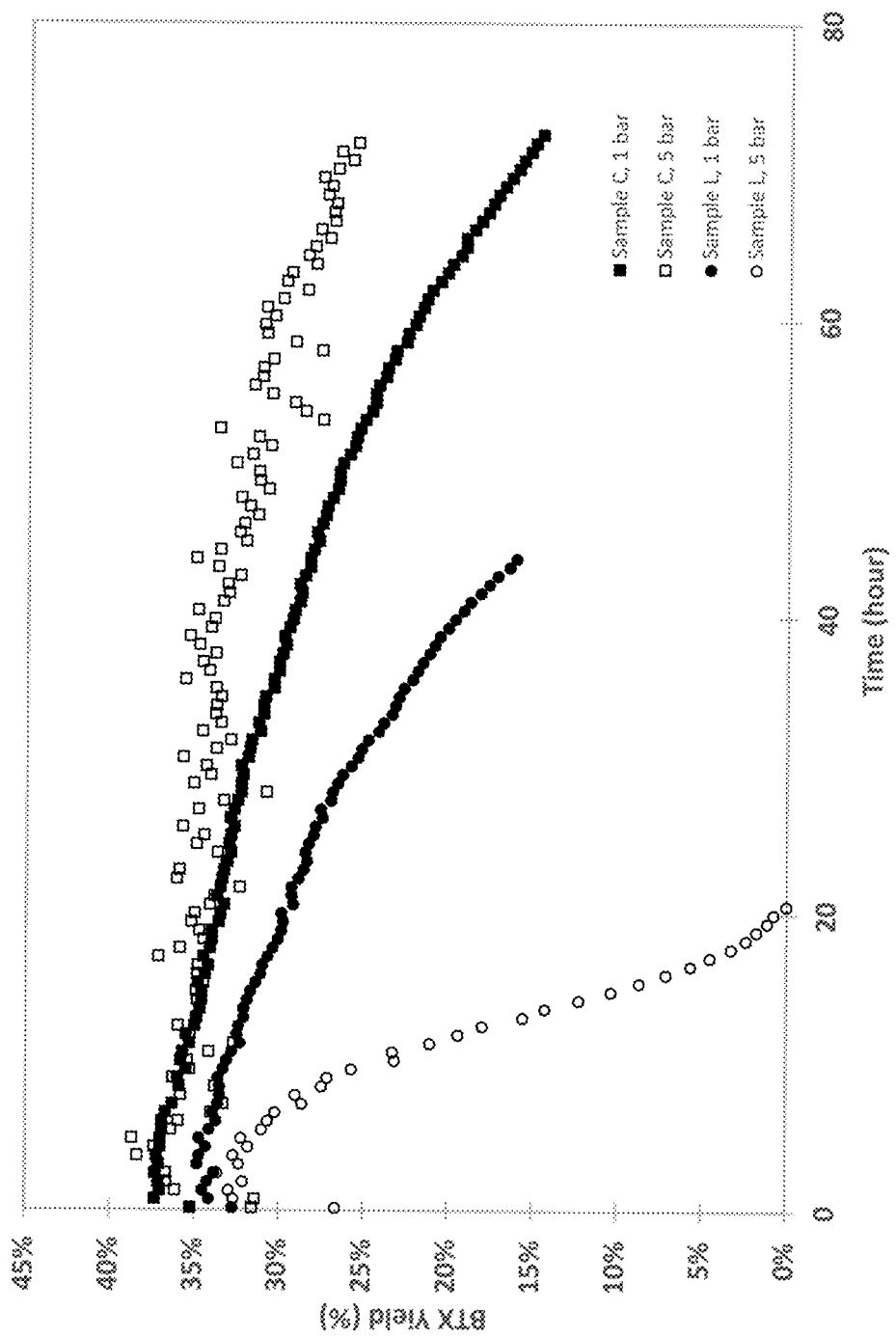
FIGS. 6A and 6B show the BTX yield over TOS and the methane selectivity over the ethylene breakthrough, respectively, at different pressure conditions for nickel phosphide catalyst (Sample C) in comparison with the metal-free (Sample L) catalyst in accordance with some embodiments.

FIG. 6A shows the BTX yield over time at the different pressures for the nickel phosphide containing catalyst (Sample C) and the metal-free catalyst (Sample L). For the metal-free catalyst (Sample L), with both samples starting at similar initial BTX yield, the increase in pressure from 1 bar to 5 bar has no effect on BTX yield but a detrimental effect on catalyst lifetime. This is seen in the sharp decline at 5 bar, increasing pressure for the metal-free catalyst decreases catalyst lifetime. In comparison, the nickel phosphide catalyst (Sample C) also have similar initial BTX yield and has a positive effect on catalyst lifetime. As seen with the 5 bar sample, the catalyst lifetime is extended at higher pressure, thus, increased pressure increases catalyst stability for the nickel phosphide catalyst.

Figure 6B:
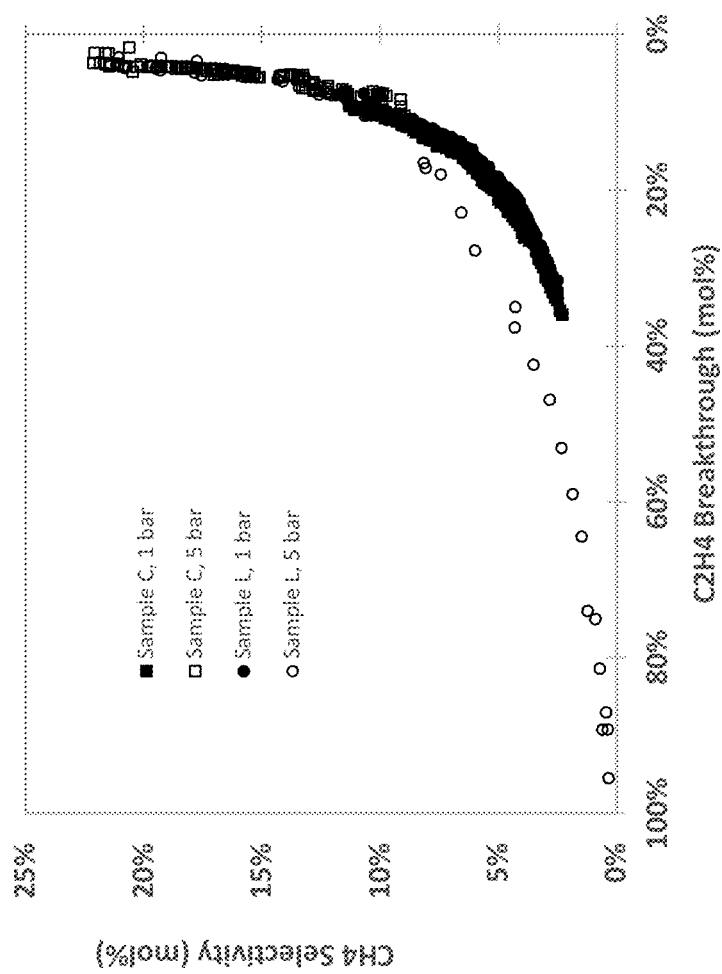

FIG. 6B shows the $CH_4$ selectivity over $C_2H_4$ breakthrough. A lower $C_2H_4$ breakthrough may indicate more $C_2H_4$ feed has been converted, either to $CH_4$ or more aromatics.

Example 15

The results for the effect of gas hourly space velocity (GHSV) on BTX and byproducts for single cycle lifetime were obtained at GHSV of 2000 and 4000 $mL_C/g_{cat}$*hr, temperature fixed at 550° C., and pressure at 3 bar for the nickel phosphide containing catalyst (Sample C) and the metal-free catalyst (Sample L). The metal-free at GHSV of 4000 $mL_C/g_{cat}$*hr was tested at 500° C. and 3 bar. All conditions were tested with a gas mixture of $C_2H_6$—$C_2H_4$—$H_2$—$N_2$ in a volume ratio of 0.67:1:1:1. All data values were calculated based on ethane.

Figure 7:
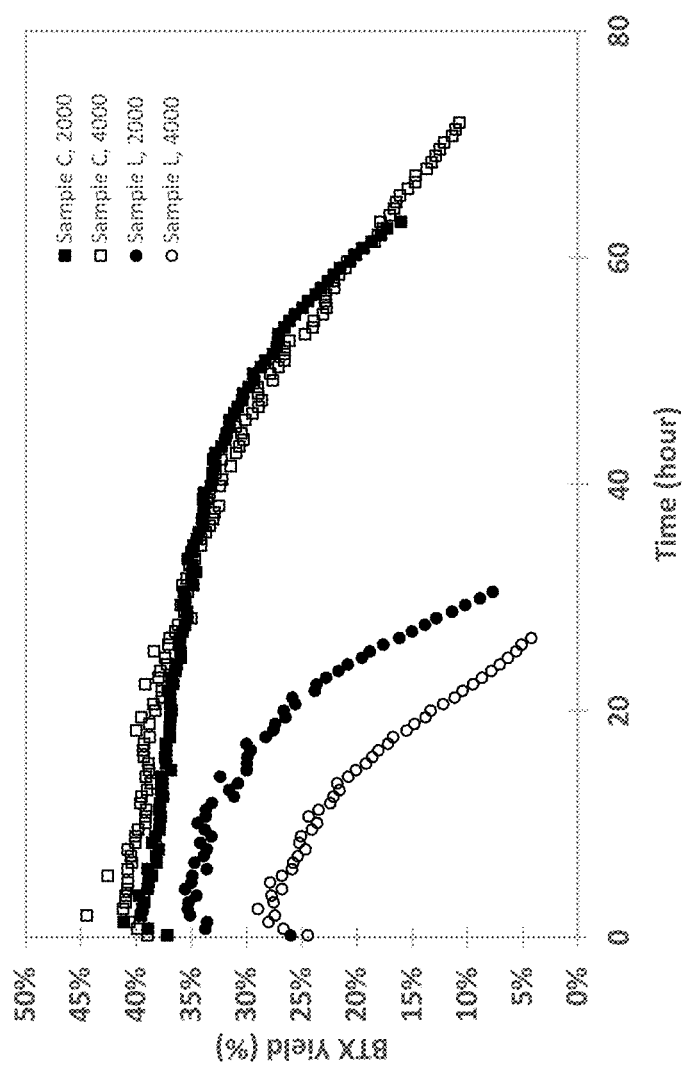
FIG. 7 shows the BTX yield over TOS for Sample C (NiP/ZSM-5) and Sample L (metal-free) catalysts for GHSV screening test in accordance with some embodiments.

FIG. 7 shows the BTX yield for different GHSV values. The nickel phosphide sample (Sample C) performs better than the metal-free catalyst (Sample L) under all GHSV as well as maintaining a higher catalyst stability.

Example 16

Tests were performed to compare different synthesis methods for NiP/ZSM-5: Sample C with a dry and physical mix, and Sample K with a wet aqueous impregnation, both using the same nickel-phosphate precursor. Both catalysts were evaluated under the same conditions at a fixed temperature, pressure, and gas-hour space velocities of 550° C., 1 bar, and GHSV=2000 $mL_C/g_{cat}$*hr, respectively. The catalysts were tested with a mixed feed of $C_2H_6:C_2H_4:H_2:N_2$ in a ratio of 0.67:1:1:1. All data values were calculated based on ethane.

Figure 8A:
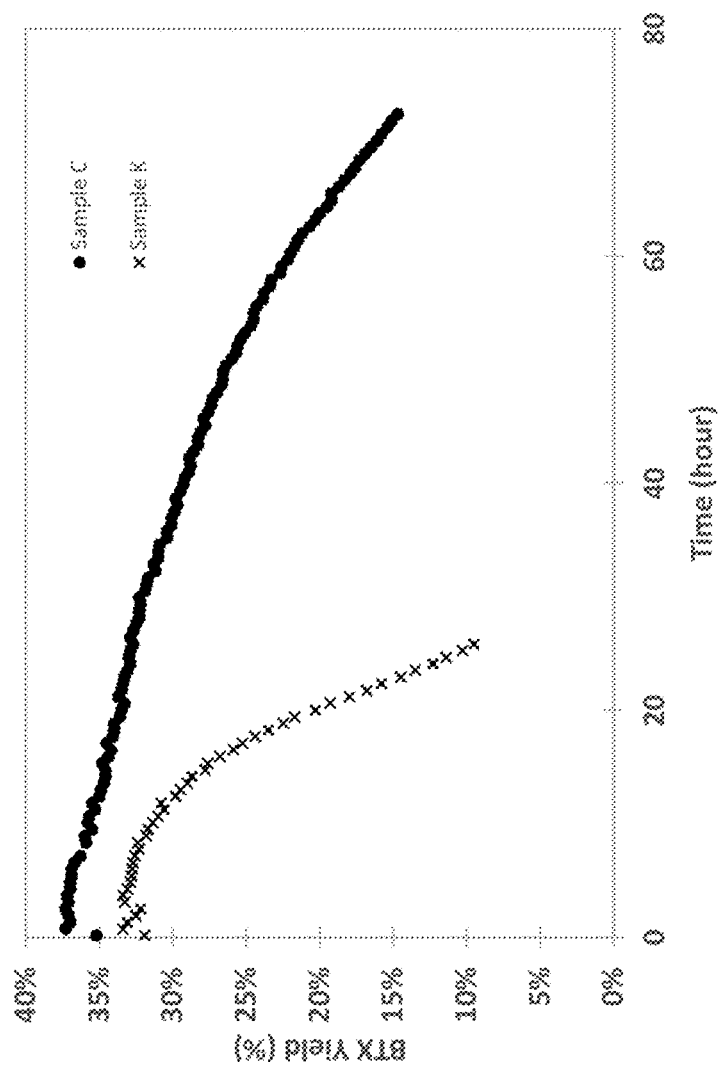
FIGS. 8A and 8B show the BTX yield over TOS and the methane selectivity over the ethylene breakthrough, respectively, for dry NiP/ZSM-5 synthesis (Sample C) and wet impregnation of NiP/ZSM-5 (Sample K) catalysts in accordance with some embodiments.
Figure 8B:
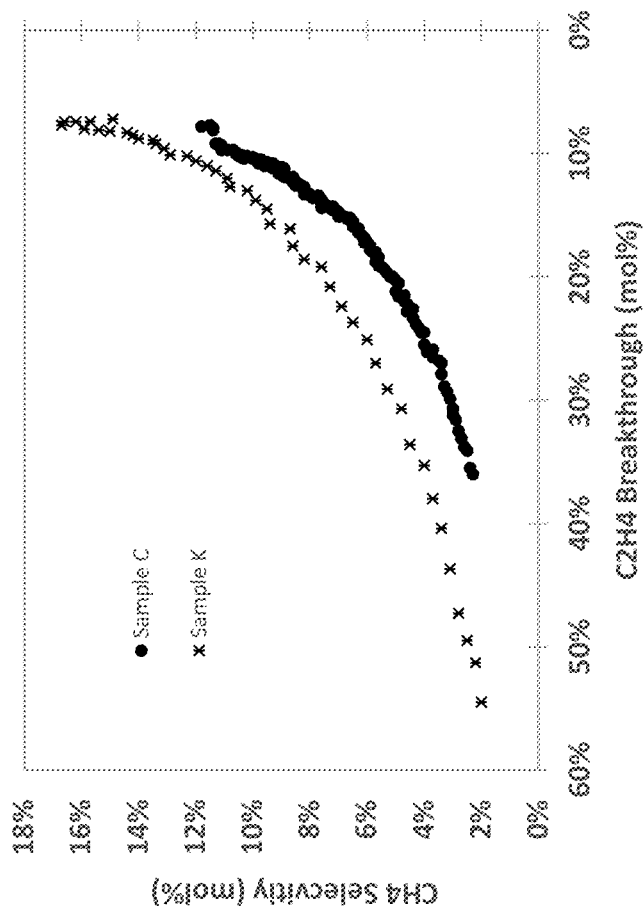

As seen in FIG. 8A, the catalyst (Sample K) containing nickel phosphide made from a wet impregnation does not provide a high BTX yield or a significant catalyst lifetime. The catalyst (Sample C) made from the dry physical mix has higher BTX yield and better catalyst stability than sample K from the wet impregnation. Sample K deactivates at 12 hours on stream while Sample C exhibits a relatively stable lifetime and deactivates around the 45-hour mark. FIG. 8B shows the $CH_4$ selectivity over $C_2H_4$ breakthrough. A lower $C_2H_4$ breakthrough may indicate more $C_2H_4$ feed has been converted, either to $CH_4$ or more aromatics.

The higher $CH_4$ selectivity for Sample K as compared to Sample C is attributed to the formation of Ni sites using the wet impregnation synthesis method followed by reduction. Sample C, made form the dry physical mix, shows a more efficient conversion of the feed, as seen in FIG. 8B.

Example 17

Sample O as an experimental extruded catalyst containing nickel phosphide, ZSM-5, and binder that was evaluated and compared to Sample L as a comparative catalyst, which is metal-free (MF). The reactions were performed at fixed temperature (550° C.), pressure (1 bar), and gas hourly space velocity (2000 $mL_C/g_{cat}$*hr), respectively. The catalysts were tested with a mixed feed of $C_2H_6:C_2H_4:H_2:N_2$ in a ratio of 0.67:1:1:1. All data values were calculated based on ethane.

Figure 9A:
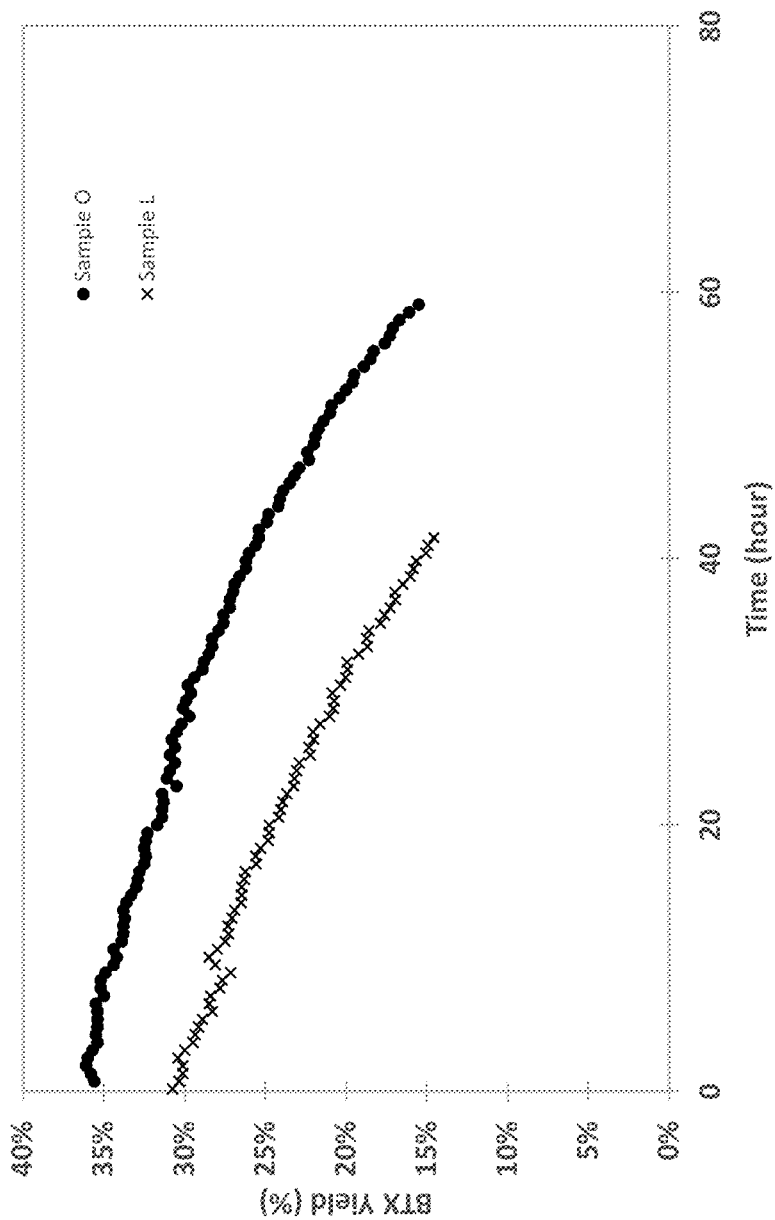
FIGS. 9A and 9B show the BTX yield over TOS and the methane selectivity over ethylene breakthrough, respectively, for a nickel phosphide catalyst (Sample O) and metal-free catalyst (Sample L) at 550° C.
Figure 9B:
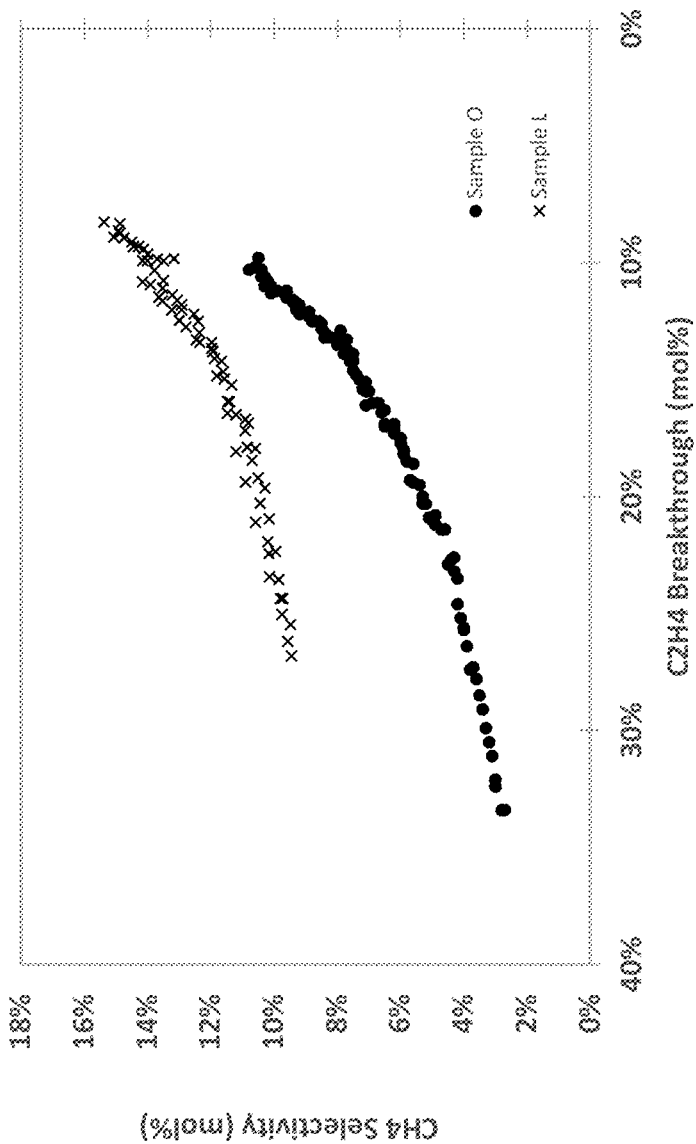

As seen in FIG. 9A, the nickel phosphide catalyst (Sample O) outperforms the metal-free catalyst (Sample L), both containing binder. The addition of nickel phosphide increases BTX yield. Additionally, FIG. 9B, which showing the $CH_4$ selectivity over $C_2H_4$ breakthrough, further shows the benefit of nickel phosphide (Sample O) over a metal-free catalyst (Sample L). FIG. 9B indicates that the nickel phosphide catalyst converts more of the feed to BTX, further supporting the data seen in FIG. 9A. In comparison, the metal-free catalyst (Sample L) has a higher $CH_4$ selectivity for any given $C_2H_4$ breakthrough value, indicating that the addition of metal phosphide more effectively converts the feed to BTX, even with the addition of a binder to the catalyst.

The catalysts containing a zeotype material, a binder, and a metal phosphide provides a high BTX product yield, a long catalyst lifetime, and a good long-term stability. For example, some catalysts provide an initial BTX yield above 30% or 35%, and maintains a BTX yield above 25% or 30% after 40 hours of use.

Although the subject matter has been described in terms of exemplary embodiments, it is not limited thereto. Rather, the appended claims should be construed broadly, to include other variants and embodiments, which may be made by those skilled in the art.

What is claimed is:

1. A catalyst for converting alkene or alkane into aromatics, comprising:
   a zeotype material being microporous;
   a binder in a range of from 0 to 50% by weight of a total weight of the catalyst; and
   a metal phosphide in a range of from 0.01% to 10% by weight of a total weight of the catalyst, wherein the metal phosphide comprises a phosphide of Ni.

2. The catalyst of claim 1, wherein the catalyst is configured to convert an olefin-containing hydrocarbon comprising at least one alkene into an aromatic hydrocarbon selected from the group consisting of benzene, toluene, xylenes, and a combination thereof, wherein the at least one alkene is selected from the group consisting of ethylene, propylene, butylene, and a combination thereof.

3. The catalyst of claim 1, wherein the zeotype material is selected from the group consisting of an alumino-silicate zeolite, an alumino-phosphate (ALPO) molecular sieve, a silico-alumino-phosphate (SAPO) molecular sieve, a metallo-alumino-phosphate (MeAPO) molecular sieve, and a combination thereof.

4. The catalyst of claim 1, wherein the zeotype material has a framework selected from MFI, MTW, MEL, TON, TUN, IMF, BEA, FAU, MOR, AEI, CHA, AFI, MWW, MTT, LTL, FER, EMT, and a combination thereof.

5. The catalyst of claim 1, wherein the zeotype material is ZSM-5 zeolite having a silica to alumina ratio (SAR) in a range of from 20 to 100.

6. The catalyst of claim 1, wherein the binder material is selected from the group consisting of silica, alumina, alumina-silica, zirconia, titania, aluminium phosphate, and a combination thereof.

7. The catalyst of claim 1, wherein the binder material is alumina.

8. The catalyst of claim 1, wherein the binder material is in a range of from 0.1% to 50% by weight of the total weight of the catalyst.

9. The catalyst of claim 1, wherein the metal phosphide further comprises a phosphide of a metal selected from Co, Ga, Fe, Zn, Cu, Mn, In, Sn, Mo, and a combination thereof.

10. The catalyst of claim 1, wherein the metal phosphide has an atomic ratio of metal to phosphorus in a range of from 3:1 to 0.5:1.

* * * * *